United States Patent
Nagata et al.

(10) Patent No.: US 10,751,289 B2
(45) Date of Patent: Aug. 25, 2020

(54) CORE-SHELL PARTICLES AND METHOD OF MANUFACTURING THE SAME

(71) Applicant: NATIONAL INSTITUTE OF ADVANCED INDUSTRIAL SCIENCE AND TECHNOLOGY, Chiyoda-ku, Tokyo (JP)

(72) Inventors: Fukue Nagata, Aichi (JP); Katsuya Kato, Aichi (JP); Masahiko Inagaki, Aichi (JP)

(73) Assignee: NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 0 days.

(21) Appl. No.: 15/508,094

(22) PCT Filed: Aug. 31, 2015

(86) PCT No.: PCT/JP2015/074687
§ 371 (c)(1),
(2) Date: Mar. 1, 2017

(87) PCT Pub. No.: WO2016/035750
PCT Pub. Date: Mar. 10, 2016

(65) Prior Publication Data
US 2017/0296479 A1    Oct. 19, 2017

(30) Foreign Application Priority Data
Sep. 2, 2014 (JP) ................................. 2014-178201

(51) Int. Cl.
*A61K 9/51* (2006.01)
*A61K 9/50* (2006.01)
*A61K 47/34* (2017.01)

(52) U.S. Cl.
CPC .......... *A61K 9/5115* (2013.01); *A61K 9/5089* (2013.01); *A61K 9/5153* (2013.01); *A61K 47/34* (2013.01)

(58) Field of Classification Search
None
See application file for complete search history.

(56) References Cited

U.S. PATENT DOCUMENTS

2013/0295186 A1*  11/2013  Loo .................... A61K 9/501
                                                        424/490

FOREIGN PATENT DOCUMENTS

JP   2002-241312 A    8/2002
JP   2008-143957 A    6/2008
WO   2012/071014 A1   5/2012

OTHER PUBLICATIONS

Fukue Nagata et al., "Preparation of spherical PLA/calcium phosphate composites", Preprints of Annual Meeting of The Ceramic Society of Japan, 2001, Mar. 21, 2001, pp. 271, The Ceramic Society of Japan, Tokyo, Japan.
Tatsuya Kuno et al., "Effect of ultrasonic irradiation on making core-shell PLA /calcium phosphate hybrid particles nano sized", Annual Meeting of The Ceramic Society of Japan, 2010, Mar. 22, 2010, pp. 205, The Ceramic Society of Japan, Tokyo, Japan.
Fukue Nagata et al., "Particle size control of apatite/polymer microsphere", Preprints of Annual Meeting of The Ceramic Society of Japan, 2002, Mar. 24, 2002, pp. 80, The Ceramic Society of Japan, Tokyo, Japan.
Vukomanovic, Marija et al., Poly (D, L-lactide-co-glycolide)/hydroxyapatite core-shell nanospheres. Part 1: A multifunctional system for controlled drug delivery., Colloids and surfaces. B, Biointerfaces, 2011, vol. 82, p. 404-413.
International Search Report in PCT/JP2015/074687, dated Oct. 13, 2015.
Extended European Search Report in EP Application No. 15837464.5, dated Dec. 22, 2017, 8pp.

* cited by examiner

*Primary Examiner* — Patricia Duffy
*Assistant Examiner* — Garen Gotfredson
(74) *Attorney, Agent, or Firm* — Hauptman Ham, LLP

(57) ABSTRACT

Provided are core-shell particles which are kept stable in a solvent such as water for a long period. Each core-shell particle includes a core which contains a hydrophobic polymer having an anionic group and a shell which contains calcium phosphate. At least one of calcium atoms contained in calcium phosphate is chemically bonded to a functional group derived from the anionic group. In a method of manufacturing core-shell particles each core-shell particle includes a core which contains a hydrophobic polymer and a shell which contains calcium phosphate, the method includes the steps of: mixing a water-soluble organic solution which contains a hydrophobic polymer having an anionic group with a solution which contains calcium ion so as to obtain a first mixed solution; mixing the first mixed solution with a solution which contains phosphate ions so as to obtain a second mixed solution; and stirring the second mixed solution.

9 Claims, 3 Drawing Sheets

CORE-SHELL PARTICLES AND METHOD OF MANUFACTURING THE SAME

RELATED APPLICATIONS

The present application is a National Stage of PCT International Application No. PCT/JP2015/074687, filed Aug. 31, 2015 which claims the benefit of priority from Japanese Patent Application No.2014-178201, filed Sep. 2, 2014.

TECHNICAL FIELD

The present invention relates to core-shell particles each of which includes a core containing hydrophobic polymer and a shell containing calcium phosphate, and a method of manufacturing the core-shell particles.

BACKGROUND ART

Composite fine particles each of which is formed of a polymer and an inorganic material can enhance functions thereof due to combination of different properties which the polymer and the inorganic material have respectively. Further, by holding a functional substance in the composite fine particles, the application of the composite fine particles is expanded to wide fields such as medicines and cosmetics. Recently, with the sharp rise of environment awareness, a biomass raw material polymer such as a polylactic acid which is produced using a renewable resource such as plants as a raw material has been attracting attention. A polylactic acid is a material which is safely metabolically degradable in vivo. Calcium phosphate which is a main component of teeth and bones and has high biocompatibility has been attracting attention as a ceramic material.

Patent literature 1 discloses a spherical biodegradable polymer coated with calcium phosphate. Patent literature 2 discloses biodegradable polymer calcium phosphate composite nanoparticles. However, in the spherical biodegradable polymer coated with calcium phosphate disclosed in patent literature 1, calcium phosphate does not coat the whole surface of the spherical biodegradable polymer and hence, the spherical biodegradable polymer is not complete core-shell particles. Accordingly, even when a functional substance is encapsulated into the spherical biodegradable polymer coated with calcium phosphate, the spherical biodegradable polymer is decomposed into low molecules by hydrolysis so that the spherical biodegradable polymer cannot hold the functional material in a stable manner. In the same manner, biodegradable polymer calcium phosphate composite nanoparticles disclosed in patent literature 2 are also not complete core-shell particles so that biodegradable polymer is decomposed into low molecules by hydrolysis so that the biodegradable polymer calcium phosphate composite nanoparticles cannot hold the functional material in a stable manner.

CITATION LIST

Patent Literature

PTL 1: JP-A-2002-241312
PTL 2: JP-A-2008-143957

SUMMARY OF INVENTION

Technical Problem

It is an object of the present invention to provide core-shell particles which are kept stable in a solvent such as water for a long period.

Solution to Problem

In core-shell particles according to the present invention, each core-shell particle includes: a core which contains a hydrophobic polymer having an anionic group; and a shell which contains calcium phosphate. At least one of calcium atoms contained in calcium phosphate is chemically bonded to a functional group derived from the anionic group. A controlled release formulation according to the present invention includes: the core-shell particles according to the present invention having an average particle size of less than 50 nm; and a drug carried by each core-shell particle.

In a method of manufacturing core-shell particles each of which includes: a core which contains a hydrophobic polymer; and a shell which contains calcium phosphate according to the present invention, the method includes the steps of: mixing a water-soluble organic solution which contains a hydrophobic polymer having an anionic group with a solution which contains calcium ion to obtain a first mixed solution; mixing the first mixed solution with a solution which contains phosphate ions to obtain a second mixed solution; and stirring the second mixed solution.

Advantageous Effects of Invention

According to the present invention, it is possible to obtain core-shell particles which are kept stable in a solvent such as water for a long period.

DESCRIPTION OF EXAMPLES

Figure 1:
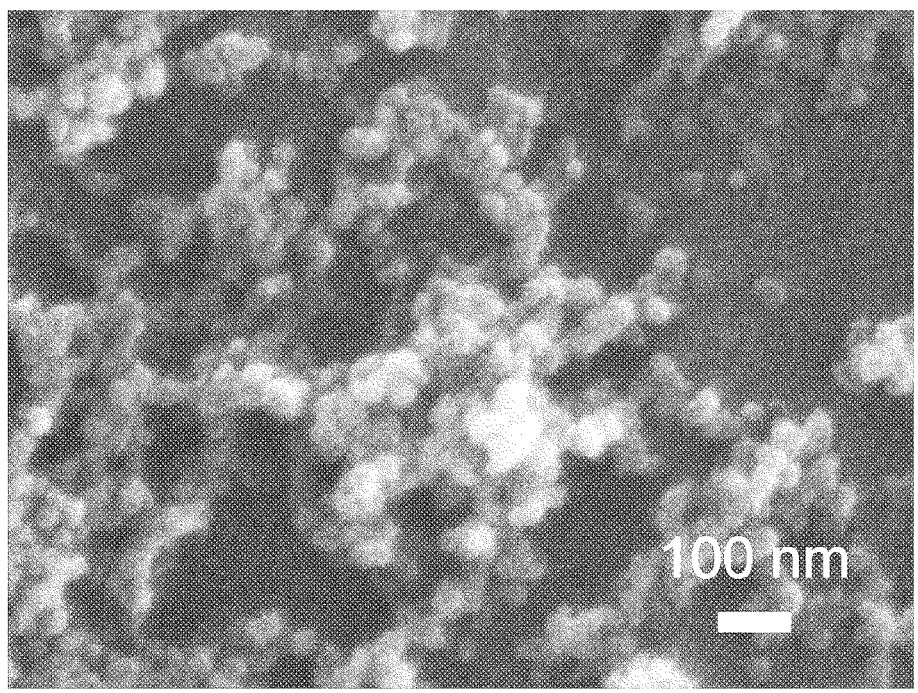
FIG. 1 is a scanning electron microscope image of core-shell particles according to an example 1.

Hereinafter, a method of manufacturing the core-shell particles, controlled release formulation and core-shell particles according to the present invention are described in conjunction with an embodiment and examples. The repeated description is omitted when necessary. When a numerical value range is expressed by putting "to" between two numerical values, these two numerical values are also included in the numerical value range.

Each of the core-shell particles according to the present invention includes: a core which contains a hydrophobic polymer having an anionic group; and a shell which contains calcium phosphate. The shell coats the whole surface of the core. An anionic group is a functional group which is charged with a negative charge when the anionic group is dissolved in a solvent such as water or a water-soluble organic solvent. As an anionic group contained in a hydrophobic polymer included in the core-shell particles according to the present invention, for example, a carboxyl group, a sulfo group, phosphate group and the like are named. However, such an anionic group is not limited to these groups. The anionic group may exist at a terminal of a hydrophobic polymer or may exist in a side chain of a hydrophobic polymer.

A hydrophobic polymer is a polymer which is not dissolved in water. It is preferable that a hydrophobic polymer contained in the core of the core-shell particle according to the present invention be dissolved in a water-soluble organic solvent. This is because, as described later, core-shell particles can be manufactured without using a surfactant. It is also preferable that a hydrophobic polymer contained in the core of the core-shell particle according to the present invention be a biodegradable polymer. This is because the biodegradable polymer is metabolically degraded safely in vivo. As a biodegradable polymer which has an anionic group, a polylactic acid, a polyglycolic acid, a lactic acid-glycolic acid copolymer and the like are named. The core of the core-shell particle according to the present invention may include two or more kinds of hydrophobic polymers.

Calcium phosphate is a salt made of calcium ion ($Ca^{2+}$) and phosphate ion ($PO_4^{3-}$) or diphosphate ion ($P_2O_7^{4-}$). As calcium phosphate included in the shell of the core-shell particle according to the present invention, for example, calcium dihydrogen phosphate ($Ca(H_2PO_4)_2$), calcium dihydrogen phosphate monohydrate ($Ca(H_2PO_4)_2 \cdot H_2O$), calcium hydrogen phosphate ($CaHPO_4$), calcium hydrogen phosphate dihydrate ($CaHPO_4 \cdot 2H_2O$), tricalcium phosphate ($Ca_3(PO_4)_2$), octacalcium phosphate ($Ca_8H_2(PO_4)_6 \cdot 5H_2O$), hydroxyapatite ($Ca_{10}(PO_4)_6(OH)_2$) and the like are named.

It is preferable that calcium phosphate in the shell of the core-shell particle according to the present invention include hydroxyapatite. It is preferable that this hydroxyapatite have a laminate structure. Since the shell includes the laminate structure of hydroxyapatite, even when the core-shell particles exist in a solvent such as water, it is possible to prevent hydrolysis of the cores. The laminate structure may preferably be formed such that hydroxyapatite is laminated in a c-axis direction toward an outer side of the shell. Due to lamination of hydroxyapatite in the c-axis direction toward an outer side of the shell, the shell becomes rigid so that the shell can stably hold the core and a substance which is encapsulated in the core.

The laminate structure can be controlled based on pH of a second mixed solution and a stirring time as described later. To acquire the stable core-shell particle, it is preferable that the laminate structure exist over the whole surface of the shell. For example, it is preferable that an outermost shell of the core-shell particle be formed of hydroxyapatite having the regular crystal structure. On the other hand, with respect to the core-shell particle which releases the core and a substance encapsulated in the core in a controlled manner, it is not always necessary that an outermost shell of the core-shell particle have the regular crystal structure.

In the core-shell particle according to the present invention, at least one of calcium atoms contained in calcium phosphate in the shell is chemically bonded to a functional group derived from an anionic group of a hydrophobic polymer in the core. That is, calcium which exists in an inner portion of the shell and a functional group derived from the anionic group which exists in an outer portion of the core are chemically bonded to each other. Accordingly, the core and the shell are minimally separated from each other so that the core-shell particle according to the present invention is minimally collapsed.

In this specification, "a functional group derived from an anionic group" is a functional group which is charged with a negative charge due to separation of an atom from an anionic group or due to adding of an atom to an anionic group. For example, when an anionic group is a carboxyl group (COOH), a functional group derived from the anionic group is a carboxylate group ($COO^-$). The term "chemical bonding" means mainly ionic bonding between calcium ion ($Ca^{2+}$) and a functional group derived from an anionic group.

The core-shell particle according to the present invention has an average particle size of 5 nm to 50 μm. It is preferable that the average particle size be set to 100 nm to 1000 nm, and it is more preferable that the average particle size be set to 100 nm to 200 nm. By setting the average particle size of the core-shell particle to such a value, the core-shell particles can be suitably used in applications such as cosmetics. This is because such core-shell particles possess excellent touch feeling and texture. When the core-shell particles can be dispersed in a solution, a particle size of the core-shell particle can be measured using a laser diffraction/scattering type particle size distribution measuring device so that a volume-based average particle size can be calculated. In the case of the core-shell particle whose average particle size cannot be easily measured by the laser diffraction/scattering type particle size distribution measuring device, a number average particle size can be calculated by measuring the sizes of particles by an electron microscope image. The average particle size of the core-shell particles according to the present invention is a volume-based average particle size or a number average particle size. A hydrophobic polymer in the core may further encapsulate a hydrophobic substance. As a hydrophobic substance, for example, a beauty promoting substance, an antibacterial substance, a pigment, a functional substance such as a functional polymer and the like are named.

When the core-shell particle according to the present invention has an average particle size of less than 50 nm, the core-shell particle is suitable as a drug delivery carrier. This is because the core-shell particle according to the present invention easily permeates a skin when the core-shell particle is used for transdermal administration of the drug. In the core-shell particle according to the present invention, a drug can be carried by the core and protein is carried by the shell. Further, the core-shell particles according to the present invention can exist in a solvent such as water for a long period. Accordingly, controlled release or targeting of a drug can be realized. That is, a controlled release formulation according to the present invention includes the core-shell particles according to the present invention and a drug carried by the core-shell particles.

A method of manufacturing core-shell particles according to the present invention includes: a step of obtaining a first mixed solution; a step of obtaining a second mixed solution; and a step of stirring the second mixed solution. In the step of obtaining the first mixed solution, the first mixed solution is obtained by mixing a water-soluble organic solution which contains a hydrophobic polymer having an anionic group and a solution which contains calcium ion. In this step, even when a surfactant or an emulsifier is not used, the water-soluble organic solution which contains the hydrophobic polymer having the anionic group and the solution which contains calcium ion are uniformly mixed with each other. Accordingly, the manufacturing method of the present invention can obtain core-shell particles containing neither a surfactant nor an emulsifier. On the other hand, in composite fine particles obtained by using a surfactant or an emulsifier, the surfactant or the emulsifier remains. It is reported that a surfactant or an emulsifier causes allergic symptoms or has a possibility of generating carcinogen.

In the step of obtaining the first mixed solution, an average particle size of the obtained core-shell particles can be controlled by adjusting concentration of hydrophobic polymer in a water-soluble organic solution which contains the hydrophobic polymer. There is a tendency for an average particle size of the obtained core-shell particles to be increased when the concentration of the hydrophobic polymer is increased. In the step of obtaining the first mixed solution, it is preferable that a ratio of a volume of a solution which contains calcium ion to a volume of a water-soluble organic solution which contains a hydrophobic polymer be 1 or more.

A water-soluble organic solution which contains a hydrophobic polymer and a solution which contains calcium ion can be mixed with each other by stirring using a propeller-type stirrer, a magnetic stirrer or the like. In this case, a mixing time is, for example, 10 seconds to 30 minutes. In the step of obtaining a first mixed solution, after a water-soluble organic solution which contains a hydrophobic polymer and a solution which contains calcium ion are mixed with each other, concentration of calcium ion is adjusted by further adding a solution which contains calcium ion. There is a tendency for an average particle size of the obtained core-shell particles to be reduced when concentration of calcium ion is increased.

When a water-soluble organic solution which contains hydrophobic polymer which has an anionic group and a solution which contains calcium ion are mixed with each other, a functional group derived from an anionic group and calcium ion are chemically bonded to each other. As a water-soluble organic solvent which is a solvent of a water-soluble organic solution, acetone, methyl ethyl ketone, dioxane, tetrahydrofuran, ethanol, methanol, propanol and the like are named. However, the water-soluble organic solvent is not particularly limited. Two or more kinds of water-soluble organic solvents may be used. Among these water-soluble organic solvents, it is preferable to use acetone. This is because acetone has a low boiling point and a hydrophobic polymer is easily dissolved in acetone.

In the manufacture of core-shell particles where a hydrophobic substance is further encapsulated in a hydrophobic polymer in the core, the hydrophobic substance may be dissolved or dispersed in a water-soluble organic solvent together with a hydrophobic polymer. That is, in the step of obtaining a first mixed solution, a water-soluble organic solution which contains a hydrophobic polymer which has an anionic group and a hydrophobic substance and a solution which contains calcium ion are mixed with each other. When the core-shell particles are used as a drug delivery carrier, hydrophobic substance encapsulated in a hydrophobic polymer in the core is an anti-cancer drug, antibiotics, an antibacterial drug, an anti-inflammatory drug, a narcotic or the like. An average particle size of obtained core-shell particles changes corresponding to a mass of a hydrophobic substance to be dissolved or dispersed.

A solution which contains calcium ion is preferably an aqueous solution. As the aqueous solution which contains calcium ion, a calcium nitride tetrahydrate aqueous solution, a calcium chloride aqueous solution, a calcium chloride monohydrate aqueous solution, a chloric acid calciumdihydrate aqueous solution, a perchloric acid calcium aqueous solution, an oxalate calcium aqueous solution, a calcium acetate aqueous solution and the like are named. However, a solution which contains calcium ion is not particularly limited. The concentration of calcium ion in the solution which contains the calcium ion is, for example, $2 \times 10^{-3}$ mol/L or less. It is preferable that the concentration of calcium ion in the solution which contains the calcium ion be, for example, $1 \times 10^{-3}$ mol/L to $2 \times 10^{-3}$ mol/L or less. This is because calcium phosphate can be regularly precipitated on a surface of a hydrophobic polymer.

In the step of obtaining a second mixed solution, the second mixed solution is obtained by mixing a first mixed solution and a solution which contains phosphate ion with each other. As a method of mixing the first mixed solution and the solution which contains phosphate ion with each other, it is preferable to drop the solution which contains phosphate ion into the first mixed solution. This is because calcium phosphate can be uniformly precipitated on a surface of a hydrophobic polymer contained in the first mixed solution. In this case, calcium phosphate is precipitated using calcium ion which is chemically bonded to a functional group derived from an anionic group of a hydrophobic polymer as a nucleus forming site and hence, sphericalization of core-shell particles is promoted.

A solution which contains phosphate ion is preferably an aqueous solution. As the aqueous solution which contains phosphate ion, a diammonium hydrogen phosphate aqueous solution, an ammonium dihydrogen phosphate aqueous solution, a disodium hydrogen phosphate aqueous solution, a sodium phosphate dihydrogen monohydrate aqueous solution, a sodium phosphate dihydrogen dihydrate aqueous solution, a potassium phosphate aqueous solution, a dipotassium phosphate hydrogen aqueous solution, a potassium phosphate dihydrogen aqueous solution, a phosphate aqueous solution and the like are named. However, the aqueous solution which contains phosphate ion is not particularly limited.

In the step of obtaining a second mixed solution, it is preferable that a ratio of a substance amount of calcium ion in a first mixed solution to a substance amount of phosphate ion in a solution which contains phosphate ion, that is, a so-called molar ratio be 0.8 to 20. This is because hydroxyapatite which is a most stable phase of calcium phosphate is likely to be precipitated when a molar ratio of calcium ion to phosphate ion is 1.7 and a molar ratio of calcium ion to phosphate ion in the first mixed solution is approximately 1.7. Even in the case where this molar ratio in the first mixed solution is higher than 1.7, when calcium phosphate is precipitated by spending a long time, most of the precipitated calcium phosphate is hydroxyapatite.

In the step of stirring a second mixed solution, the second mixed solution can be stirred using a stirrer such as a propeller stirrer or a magnetic stirrer. Through the step of stirring the second mixed solution, it is possible to obtain core-shell particles dispersed in the second mixed solution. In the case where the second mixed solution contains a water-soluble organic solvent and water, it is possible to evaporate the water-soluble organic solvent due to the stirring of the second mixed solution. Further, due to the stirring of the second mixed solution, the distribution of concentration of the second mixed solution becomes uniform. Accordingly, it is possible to obtain a particles-in-water dispersion solution which contains core-shell particles having substantially the same particle size at the time of completion of stirring. This particles-in-water dispersion solution is subjected to solid-solution separation by filtering, centrifugal separation, freeze drying or the like. Core-shell particles can be separated from the particles-in-water dispersion solution by solid-solution separation.

In the step of stirring a second mixed solution, the crystal structure of an outermost shell of each core-shell particle can be changed by changing pH of the second mixed solution and a stirring time of the second mixed solution. To be more specific, in the manufacture of core-shell particles where a core and a substance which is encapsulated in the core are released in a controlled manner, the second mixed solution is preferably stirred in a state where pH is set to 8 or less, and a stirring time is preferably set to 1 to 120 hours, and is more preferably set to 3 to 72 hours, for example. On the other hand, in the manufacture of stable core-shell particles, the second mixed solution is preferably stirred in a state where pH is set to 9 or more, and a stirring time is preferably set to 72 hours or more for accelerating the precipitation of a calcium phosphate on a surface of a hydrophobic polymer. The method of manufacturing core-shell particles according to the present invention can be performed at a room temperature and at a normal pressure and hence, it is possible to suppress the degeneration of a hydrophobic polymer and a hydrophobic substance which is functional substance in the core. Further, the method of manufacturing core-shell particles according to the present invention can be performed at a room temperature and at a normal pressure and hence, a load applied to an environment can be reduced.

EXAMPLES

Next, the present invention is specifically described in conjunction with examples. However, the present invention is not limited to the examples. Particle sizes and an average particle size of core-shell particles are measured and calculated using a laser diffraction/scattering type particle size distribution measuring device or a scanning electron microscope image.

Example 1

First, 0.01 g of polylactic acid having a weight average molecular weight of 20000 is dissolved in 2 mL of acetone. Next, the acetone solution is added to 180 mL of calcium acetate aqueous solution having $2\times10^{-3}$ mol/L, and the aqueous solution is stirred at 500 rpm for 5 minutes using a magnetic stirrer so that a first mixed solution is obtained. Then, 20 mL of diammonium hydrogen phosphate aqueous solution having 0.012 mol/L is dropped into the first mixed solution while stirring the first mixed solution at 500 rpm using the magnetic stirrer so that a second mixed solution is obtained. pH of the second mixed solution is 8 or less. Then, acetone is evaporated while stirring the second mixed solution at 500 rpm for 48 hours using the magnetic stirrer so that a core-shell particle dispersion liquid is obtained. Next, this dispersion liquid is subjected to filtering and, thereafter, is subjected to freeze drying so that core-shell particles are obtained.

FIG. 1 is a scanning electron microscope image of the core-shell particles according to the example 1. As shown in FIG. 1, a large number of core-shell particles having a particle size of approximately 30 nm are observed. A maximum particle size of the core-shell particles is 40 nm. It is also confirmed from a powder X-ray diffraction spectrum that core-shell particle according to the example 1 contains hydroxyapatite. Further, it is confirmed from a transmission electron microscope image that the core-shell particle according to the example 1 has a core and a shell. When an FT-IR analysis is applied to the core-shell particle according to the example 1, a peak of 3580 cm$^{-1}$ attributed to O—H stretching vibration of a terminal COOH group of a polylactic acid is not found. From this result, it is considered that a COO$^-$ group is formed due to the separation of H from the terminal COOH group of the polylactic acid, and hydroxyapatite is precipitated using the COO$^-$ group as a nucleus forming site.

Example 2

First, 0.02 g of polylactic acid having a weight average molecular weight of 20000 is dissolved in 4 mL of acetone. Next, the acetone solution is added to 180 mL of calcium acetate aqueous solution having $2\times10^{-3}$ mol/L, and the aqueous solution is stirred at 500 rpm for 5 minutes using a magnetic stirrer so that a first mixed solution is obtained. Then, 20 mL of diammonium hydrogen phosphate aqueous solution having 0.012 mol/L is dropped into the first mixed solution while stirring the first mixed solution at 500 rpm using the magnetic stirrer so that a second mixed solution is obtained. The pH of the second mixed solution is 8 or less. Then, acetone is evaporated while stirring the second mixed solution at 500 rpm for 72 hours using the magnetic stirrer so that a core-shell particle dispersion liquid is obtained. Next, this dispersion liquid is subjected to filtering and, thereafter, is subjected to freeze drying so that core-shell particles are obtained.

Figure 2:
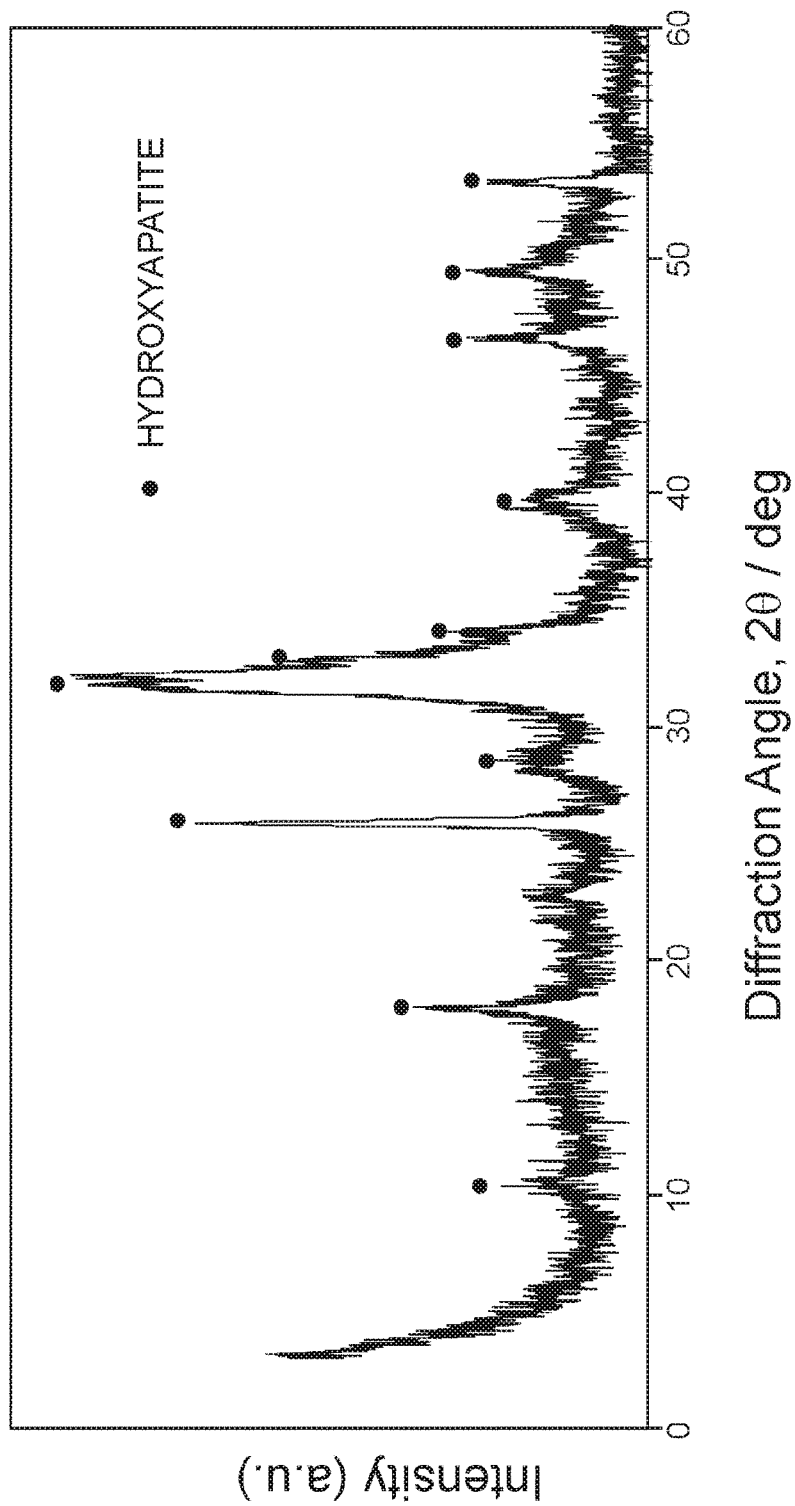
FIG. 2 is a powder X-ray diffraction spectrum of core-shell particles according to an example 2.
Figure 3:
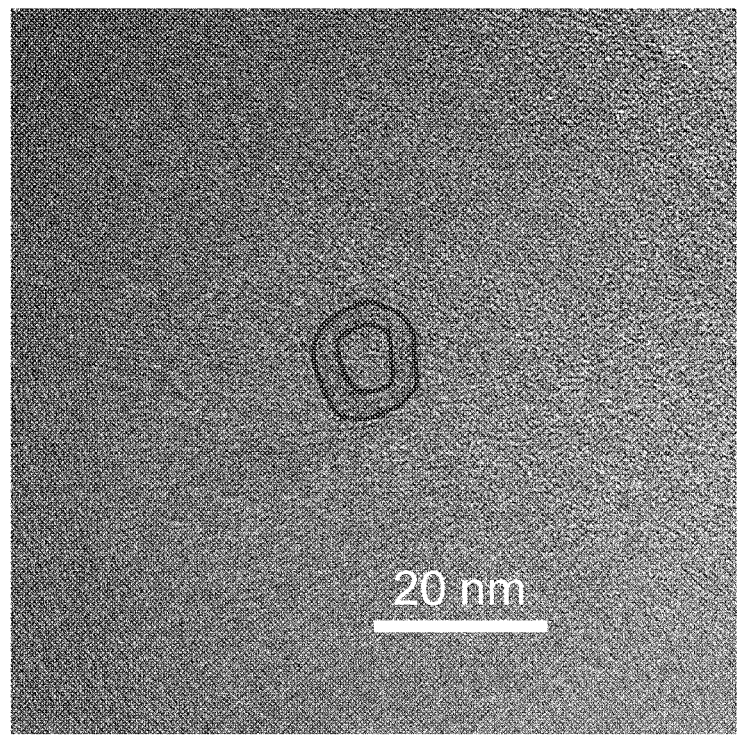
FIG. 3 is a transmission electron microscope image of the core-shell particles according to the example 2.

According to a scanning electron microscope image of the core-shell particles according to the example 2, a large number of core-shell particles having a particle size of approximately 30 nm are observed. A maximum particle size of the core-shell particles is 45 nm. FIG. 2 shows a powder X-ray diffraction spectrum of core-shell particles according to the example 2. As shown in FIG. 2, the powder X-ray diffraction spectrum agrees well with a diffraction peak of hydroxyapatite and hence, it is found that each of the core-shell particles according to the example 2 contains hydroxyapatite. FIG. 3 is a transmission electron microscope image of the core-shell particles according to the example 2. In FIG. 3, a black line is inserted into outer peripheries of a core and a shell. As shown in FIG. 3, it is found that the core-shell particle according to the example 2 contains the core and the shell. Further, from a lattice image obtained by a transmission electron microscope, it is found that hydroxyapatite is laminated in a c-axis direction toward an outer side of the shell.

Comparative Example 3

First, 0.4 g of polylactic acid having a weight average molecular weight of 20000 is dissolved in 40 mL of acetone. Next, the acetone solution is added to 600 mL of calcium acetate aqueous solution having $1\times10^{-2}$ mol/L, and the aqueous solution is stirred at 100 rpm for 3 minutes using a magnetic stirrer so that a first mixed solution is obtained. Then, 200 mL of diammonium hydrogen phosphate aqueous solution having 0.012 mol/L is dropped into the first mixed solution while stirring the first mixed solution at 100 rpm using the magnetic stirrer so that a second mixed solution is obtained. pH of the second mixed solution is 8 or less.

Then, acetone is evaporated while stirring the second mixed solution at 100 rpm for 24 hours using the magnetic stirrer so that a composite nanoparticle dispersion liquid is obtained. Next, this dispersion liquid is subjected to filtering and, thereafter, is subjected to freeze drying so that composite nanoparticles are obtained. From a scanning electron microscope image, it is confirmed that an average particle size of the composite nanoparticles according to the comparative example 3 is 50 nm. It is also confirmed from a powder X-ray diffraction spectrum that the composite nanoparticle contains hydroxyapatite.

Example 4

First, 0.02 g of polylactic acid having a weight average molecular weight of 20000 and 0.0001 g of β-carotene are dissolved in 4 mL of acetone. Next, the acetone solution is added to 180 mL of calcium acetate aqueous solution having $2\times10^{-3}$ mol/L, and the aqueous solution is stirred at 500 rpm for 5 minutes using a magnetic stirrer so that a first mixed solution is obtained. Then, 20 mL of diammonium hydrogen phosphate aqueous solution having 0.012 mol/L is dropped into the first mixed solution while stirring the first mixed solution at 500 rpm using the magnetic stirrer so that a second mixed solution is obtained. pH of the second mixed solution is 8 or less.

Then, acetone is evaporated while stirring the second mixed solution at 500 rpm for 72 hours using the magnetic stirrer so that a core-shell particle controlled release formulation dispersion liquid is obtained. Next, this dispersion liquid is subjected to filtering and, thereafter, is subjected to freeze drying so that controlled release formulation is obtained. The obtained controlled release formulation exhibits orange which is a characterizing color of β-carotene. Accordingly, it is found that the controlled release formulation is a formulation where β-carotene is carried by the core shell fine particle.

Example 5

First, 4 mg of polylactic acid having a weight average molecular weight of 20000 and 7.5 mg of vitamin $K_1$ are dissolved in 0.7 mL of acetone. Next, the acetone solution is added to 50 mL of calcium acetate aqueous solution having $1.6\times10^{-3}$ mol/L, and the aqueous solution is stirred at 500 rpm for 5 minutes using a magnetic stirrer so that a first mixed solution is obtained. Then, 0.04 mL of diammonium hydrogen phosphate aqueous solution having 1.2 mol/L is dropped into the first mixed solution while stirring the first mixed solution at 500 rpm using the magnetic stirrer so that a second mixed solution is obtained. Next, 25% ammonia water is dropped into the second mixed solution little by little so as to adjust pH of the second mixed solution to 10.

Then, acetone is evaporated while stirring the second mixed solution at 500 rpm for 96 hours using the magnetic stirrer so that a core-shell particle dispersion liquid is obtained. Next, this dispersion liquid is subjected to filtering and, thereafter, is subjected to freeze drying so that core-shell particles are obtained. When particle sizes of the core-shell particles according to the example 5 are measured using a laser diffraction/scattering type particle size distribution measuring device, an average particle size is 0.5 µm, a median diameter (D50) is 0.4 µm, 10% diameter (D10) is 0.3 µm, and 90% diameter (D90) is 0.7 µm. The obtained composite fine particles exhibit yellow which is a characterizing color of vitamin $K_1$ and hence, it is found that the core-shell particle according to the example 5 contains vitamin $K_1$.

Example 6

First, 4 mg of polylactic acid having a weight average molecular weight of 20000 and 15 mg of vitamin $K_1$ are dissolved in 1.2 mL of acetone. Next, the acetone solution is added to 50 mL of calcium acetate aqueous solution having $1.6\times10^{-3}$ mol/L, and the aqueous solution is stirred at 500 rpm for 5 minutes using a magnetic stirrer so that a first mixed solution is obtained. Then, 0.04 mL of diammonium hydrogen phosphate aqueous solution having 1.2 mol/L is dropped into the first mixed solution while stirring the first mixed solution at 500 rpm using the magnetic stirrer so that a second mixed solution is obtained. Next, 25% ammonia water is dropped into the second mixed solution little by little so as to adjust pH of the second mixed solution to 10.

Then, acetone is evaporated while stirring the second mixed solution at 500 rpm for 96 hours using the magnetic stirrer so that a core-shell particle dispersion liquid is obtained. Next, this dispersion liquid is subjected to filtering and, thereafter, is subjected to freeze drying so that core-shell particles are obtained. When particle sizes of the core-shell particles according to the example 6 are measured using a laser diffraction/scattering type particle size distribution measuring device, an average particle size is 1.4 µm, a median diameter (D50) is 1.3 µm, 10% diameter (D10) is 0.8 µm, and 90% diameter (D90) is 2.1 µm. The obtained composite fine particles exhibit yellow which is a characterizing color of vitamin $K_1$ and hence, it is found that the core-shell particle according to the example 6 contains vitamin $K_1$.

Example 7

First, 4 mg of polylactic acid having a weight average molecular weight of 20000 and 30 mg of vitamin $K_1$ are dissolved in 2.2 mL of acetone. Next, the acetone solution is added to 50 mL of calcium acetate aqueous solution having $1.6\times10^{-3}$ mol/L, and the aqueous solution is stirred at 500 rpm for 5 minutes using a magnetic stirrer so that a first mixed solution is obtained. Then, 0.04 mL of diammonium hydrogen phosphate aqueous solution having 1.2 mol/L is dropped into the first mixed solution while stirring the first mixed solution at 500 rpm using the magnetic stirrer so that a second mixed solution is obtained. Next, 25% ammonia water is dropped into the second mixed solution little by little so as to adjust pH of the second mixed solution to 10.

Then, acetone is evaporated while stirring the second mixed solution at 500 rpm for 96 hours using the magnetic stirrer so that a core-shell particle dispersion liquid is obtained. Next, this dispersion liquid is subjected to filtering and, thereafter, is subjected to freeze drying so that core-shell particles are obtained. When particle sizes of the core-shell particles according to the example 7 are measured using a laser diffraction/scattering type particle size distribution measuring device, an average particle size is 5.4 µm, a median diameter (D50) is 5.4 µm, 10% diameter (D10) is 1.8 µm, and 90% diameter (D90) is 12 µm. The obtained composite fine particles exhibit yellow which is a characterizing color of vitamin $K_1$ and hence, it is found that the core-shell particle according to the example 7 contains vitamin $K_1$.

Example 8

First, 5 mg of polylactic acid having a weight average molecular weight of 10000 and 15 mg of polylactic acid having a weight average molecular weight of 20000 are dissolved in 4 mL of acetone. Next, the acetone solution is added to 220 mL of calcium acetate aqueous solution having $1.8\times10^{-3}$ mol/L, and the aqueous solution is stirred at 500 rpm for 5 minutes using a magnetic stirrer so that a first mixed solution is obtained. Then, 20 mL of diammonium hydrogen phosphate aqueous solution having 0.12 mol/L is dropped into the first mixed solution while stirring the first mixed solution at 500 rpm using the magnetic stirrer so that a second mixed solution is obtained. Next, 25% ammonia water is dropped into the second mixed solution little by little so as to adjust pH of the second mixed solution to 10.

Then, acetone is evaporated while stirring the second mixed solution at 500 rpm for 96 hours using the magnetic stirrer so that a core-shell particle dispersion liquid is obtained. Next, this dispersion liquid is subjected to filtering and, thereafter, is subjected to freeze drying so that core-shell particles are obtained. From a scanning electron microscope image, it is confirmed that an average particle size of the core-shell particles according to the example 8 is approximately 40 nm. Further, it is confirmed that the core-shell particles according to the example 8 are safe according to a skin irritancy test using a human 3-dimensional cultured skin model made by Japan Tissue Engineering Co., Ltd. (described in OECD TG439).

Example 9

First, 40 mg of polylactic acid having a weight average molecular weight of 20000 and 1.6 mg of vitamin $K_1$ are dissolved in 4 mL of acetone. Next, the acetone solution is added to 500 mL of calcium acetate aqueous solution having $1.6 \times 10^{-3}$ mol/L, and the aqueous solution is stirred at 500 rpm for 5 minutes using a magnetic stirrer so that a first mixed solution is obtained. Then, 4 mL of diammonium hydrogen phosphate aqueous solution having 0.12 mol/L is dropped into the first mixed solution while stirring the first mixed solution at 500 rpm using the magnetic stirrer so that a second mixed solution is obtained. pH of the second mixed solution is 8 or less.

Then, acetone is evaporated while stirring the second mixed solution at 500 rpm for 75 hours using the magnetic stirrer so that a core-shell particle dispersion liquid is obtained. Next, this dispersion liquid is subjected to filtering and, thereafter, is subjected to freeze drying so that core-shell particles are obtained. From a scanning electron microscope image, it is confirmed that particle sizes of the most of the core-shell particles according to the example 9 are 30 nm to 100 nm. The core-shell particles according to the example 9 are dispersed in $66 \times 10^{-3}$ mol/L phosphate buffer solution at a temperature of 37° C. After a predetermined time elapses, solid-solution separation is applied to the phosphate buffer solution using a centrifugal separator, and concentration of vitamin $K_1$ released in a supernatant solution is measured. As a result, over 30 days, a mass of vitamin $K_1$ released from the core-shell particle in a day is an approximately fixed value which is 0.03% to 0.08% of a mass of vitamin $K_1$ contained in the core-shell particle in the previous day.

Example 10

First, 40 mg of polylactic acid having a weight average molecular weight of 20000 and 0.6 mg of β-carotene are dissolved in 4 mL of acetone. Next, the acetone solution is added to 400 mL of calcium acetate aqueous solution having $1.0 \times 10^{-3}$ mol/L, and the aqueous solution is stirred at 500 rpm for 5 minutes using a magnetic stirrer so that a first mixed solution is obtained. Then, 0.2 mL of diammonium hydrogen phosphate aqueous solution having 1.2 mol/L is dropped into the first mixed solution while stirring the first mixed solution at 500 rpm using the magnetic stirrer so that a second mixed solution is obtained. Next, 25% ammonia water is dropped into the second mixed solution little by little so as to adjust pH of the second mixed solution to 10.

Figure 4:
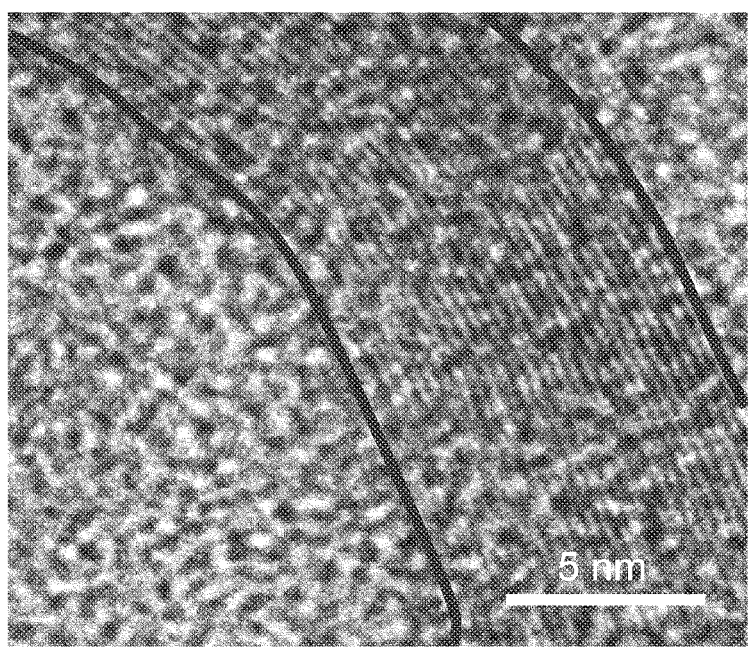
FIG. 4 is a transmission electron microscope image of a shell portion of core-shell particle according to an example 10.

Then, acetone is evaporated while stirring the second mixed solution at 500 rpm for 75 hours using the magnetic stirrer so that a core-shell particle dispersion liquid is obtained. Next, this dispersion liquid is subjected to filtering and, thereafter, is subjected to freeze drying so that core-shell particles are obtained. From a scanning electron microscope image, it is confirmed that particle sizes of the most of the core-shell particles according to the example 10 are 100 nm to 200 nm. The obtained composite fine particles exhibit orange which is a characterizing color of β-carotene and hence, it is found that the core-shell particle according to the example 10 contains β-carotene. FIG. 4 is a transmission electron microscope image of a shell portion of the core-shell particle according to the example 10. In FIG. 4, a black line is inserted into outer peripheries of a core and a shell. As shown in FIG. 4, it is confirmed that a lattice fringe of hydroxyapatite crystal exists in the shell portion of the core-shell particle according to the example 10. It is also confirmed that the hydroxyapatite crystal is regularly laminated.

Example 11

First, 20 mg of polylactic acid having a weight average molecular weight of 20000 and 0.15 mg of β-carotene are dissolved in 2 mL of acetone. Next, the acetone solution is added to 220 mL of calcium acetate aqueous solution having $1.8 \times 10^{-3}$ mol/L, and the aqueous solution is stirred at 500 rpm for 5 minutes using a magnetic stirrer so that a first mixed solution is obtained. Then, 20 mL of diammonium hydrogen phosphate aqueous solution having 0.012 mol/L is dropped into the first mixed solution while stirring the first mixed solution at 500 rpm using the magnetic stirrer so that a second mixed solution is obtained. Next, 25% ammonia water is dropped into the second mixed solution little by little so as to adjust pH of the second mixed solution to 10.

Then, acetone is evaporated while stirring the second mixed solution at 500 rpm for 96 hours using the magnetic stirrer so that a core-shell particle dispersion liquid is obtained. Next, this dispersion liquid is subjected to filtering and, thereafter, is subjected to freeze drying so that core-shell particles are obtained. From a scanning electron microscope image, it is confirmed that particle sizes of most of the core-shell particles according to the example 11 are 20 nm to 100 nm. The obtained composite fine particles exhibit orange which is a characterizing color of β-carotene and hence, it is found that the core-shell particle according to the example 11 contains β-carotene. It is also confirmed that the core-shell particles according to the example 11 is safe according to a skin irritancy test. Further, when the core-shell particles according to the example 11 are suspended in distilled water and is left to stand in a refrigerator having a temperature of 4° C., the core-shell particles hold β-carotene for 36 months.

Example 12

First, 40 mg of polylactic acid having a weight average molecular weight of 20000 and 5 mg of triclosan which is an antibacterial agent are dissolved in 4 mL of acetone. Next, the acetone solution is added to 500 mL of calcium acetate aqueous solution having $1.6 \times 10^{-3}$ mol/L, and the aqueous solution is stirred at 500 rpm for 5 minutes using a magnetic stirrer so that a first mixed solution is obtained. Then, 0.4 mL of a diammonium hydrogen phosphate aqueous solution having 1.2 mol/L is dropped into the first mixed solution while stirring the first mixed solution at 500 rpm using the magnetic stirrer so that a second mixed solution is obtained. pH of the second mixed solution is 8 or less.

Then, acetone is evaporated while stirring the second mixed solution at 500 rpm for 96 hours using the magnetic stirrer so that a core-shell particle dispersion liquid is obtained. Next, the core-shell particle dispersion liquid is subjected to filtering and, thereafter, is subjected to freeze drying so that core-shell particles are obtained. When the core-shell particles according to the example 12 is added to an agar medium to which colon bacillus is coated and the agar medium is cultured, a colony of colon bacillus does not appear. On the other hand, when an agar medium to which colon bacillus is coated is cultured under the same conditions without adding the core-shell particles according to the example 12 to the agar medium, a colony of colon bacillus is observed. Accordingly, it is found that the core-shell particles according to the example 12 suppress the increase of the number of colon bacillus.

Example 13

First, 20 mg of polylactic acid having a weight average molecular weight of 20000 and 3 mg of vitamin $K_1$ are dissolved in 4 mL of acetone. Next, the acetone solution is added to 180 mL of calcium acetate aqueous solution having $2.0 \times 10^{-3}$ mol/L, and the aqueous solution is stirred at 500 rpm for 5 minutes using a magnetic stirrer so that a first mixed solution is obtained. Then, 20 mL of diammonium hydrogen phosphate aqueous solution having 0.012 mol/L is dropped into the first mixed solution while stirring the first mixed solution at 500 rpm using the magnetic stirrer so that a second mixed solution is obtained. pH of the second mixed solution is 8 or less.

Then, acetone is evaporated while stirring the second mixed solution at 500 rpm for 48 hours using the magnetic stirrer so that a core-shell particle dispersion liquid is obtained. Next, this core-shell particle dispersion liquid is subjected to filtering and, thereafter, is subjected to freeze drying so that core-shell particles are obtained. The core-shell particles according to the example 13 are immersed in a 20 mass % of ethanol aqueous solution for 20 minutes, and an eluted amount of vitamin $K_1$ is measured. As a result, 16 mass % of vitamin $K_1$ contained in the core-shell particles according to the example 13 is eluted.

Example 14

First, 20 mg of polylactic acid having a weight average molecular weight of 20000 and 3 mg of vitamin $K_1$ are dissolved in 4 mL of acetone. Next, the acetone solution is added to 220 mL of calcium acetate aqueous solution having $1.8 \times 10^{-3}$ mol/L, and the aqueous solution is stirred at 500 rpm for 5 minutes using a magnetic stirrer so that a first mixed solution is obtained. Then, 20 mL of diammonium hydrogen phosphate aqueous solution having 0.012 mol/L is dropped into the first mixed solution while stirring the first mixed solution at 500 rpm using the magnetic stirrer so that a second mixed solution is obtained. Next, 25% ammonia water is dropped into the second mixed solution little by little so as to adjust pH of the second mixed solution to 10.

Then, acetone is evaporated while stirring the second mixed solution at 500 rpm for 73 hours using the magnetic stirrer so that a core-shell particle dispersion liquid is obtained. Next, this dispersion liquid is subjected to filtering and, thereafter, is subjected to freeze drying so that core-shell particles are obtained. The core-shell particles according to the example 14 are immersed in a 20 mass % of ethanol aqueous solution for 20 minutes, and an eluted amount of vitamin $K_1$ is measured. As a result, 5 mass % of vitamin $K_1$ contained in the core-shell particles according to the example 14 is eluted.

An eluted amount of vitamin $K_1$ in the core-shell particles according to the example 14 is ⅓ or less of an eluted amount of vitamin $K_1$ in the core-shell particles according to the example 13. It is considered that the core-shell particles according to the example 14 are manufactured by stirring the second mixed solution while adjusting pH to 9 or more and hence, the core-shell particles have the structure where hydroxyapatite crystal which forms the shell is more stable. It is also considered that the core-shell particles according to the example 14 are manufactured by stirring the second mixed solution for 72 or more hours and hence, the core-shell particle has the structure where hydroxyapatite crystal which forms the shell is more stable and, further, the number of laminated structures of hydroxyapatite is further increased.

INDUSTRIAL APPLICABILITY

The core-shell particles according to the present invention can be used as a drug delivery carrier, cosmetics and the like.

The invention claimed is:
1. Core-shell particles each comprising:
   a core which contains a hydrophobic polymer having an anionic group;
   a shell which contains calcium phosphate and coats the whole surface of the core, wherein
   at least one of calcium atoms contained in calcium phosphate is chemically bonded to a functional group derived from the anionic group,
   the calcium phosphate contains hydroxyapatite,
   the shell has a laminate structure of the hydroxyapatite, and
   the laminate structure is configured such that hydroxyapatite is laminated in a c-axis direction toward an outer side of the shell.
2. The core-shell particles according to claim 1, wherein the anionic group is a carboxyl group.
3. The core-shell particles according to claim 1, wherein the hydrophobic polymer is a biodegradable polymer.
4. The core-shell particles according to claim 3, wherein the biodegradable polymer is a polylactic acid.
5. The core-shell particles according to claim 1, wherein an average particle size of the core-shell particles is 100 nm to 1000 nm.
6. The core-shell particles according to claim 5, wherein the average particle size of the core-shell particles is 100 nm to 200 nm.
7. The core-shell particles according to claim 5, wherein a hydrophobic substance is further encapsulated in the hydrophobic polymer in the core.
8. The core-shell particles according to claim 1, wherein an average particle size of the core-shell particles is less than 50 nm, and the core-shell particles are used as a drug delivery carrier.
9. A controlled release formulation comprising:
   the core-shell particles according to claim 8; and
   a drug carried by the core-shell particle.

* * * * *